US009785741B2

(12) United States Patent
Lenchner et al.

(10) Patent No.: US 9,785,741 B2
(45) Date of Patent: Oct. 10, 2017

(54) IMMERSIVE VIRTUAL TELEPRESENCE IN A SMART ENVIRONMENT

(71) Applicant: International Business Machines Corporation, Armonk, NY (US)

(72) Inventors: Jonathan Lenchner, North Salem, NY (US); Vinay Venkataraman, Tempe, AZ (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/984,841

(22) Filed: Dec. 30, 2015

(65) Prior Publication Data
US 2017/0193711 A1 Jul. 6, 2017

(51) Int. Cl.
*G06F 19/20* (2011.01)
*G06F 3/16* (2006.01)
*G06F 3/01* (2006.01)
*H04N 5/247* (2006.01)

(52) U.S. Cl.
CPC ............. *G06F 19/20* (2013.01); *G06F 3/017* (2013.01); *G06F 3/167* (2013.01); *H04N 5/247* (2013.01)

(58) Field of Classification Search
CPC ..... G06F 3/011; G06F 3/017; G06K 9/00335; G06T 19/006
See application file for complete search history.

(56) References Cited

U.S. PATENT DOCUMENTS

| 5,769,640 | A | 6/1998 | Jacobus et al. | |
|---|---|---|---|---|
| 2009/0263775 | A1* | 10/2009 | Ullrich | G09B 23/32 434/267 |
| 2015/0012426 | A1* | 1/2015 | Purves | G06Q 30/0623 705/41 |
| 2016/0049004 | A1* | 2/2016 | Mullins | G06T 19/006 345/419 |
| 2016/0134840 | A1* | 5/2016 | McCulloch | H04N 7/157 348/14.03 |
| 2016/0140868 | A1* | 5/2016 | Lovett | G09B 19/0053 434/118 |
| 2016/0378861 | A1* | 12/2016 | Eledath | G06F 17/30828 707/766 |

OTHER PUBLICATIONS

T. Mazuryk et al., "Virtual Reality, History, Applications, Technology and Future," Institute of Computer Graphics and Algorithms, Vienna University of Technology, Technical Report TR-186-2-96-06, 1996, 72 pages.

(Continued)

*Primary Examiner* — Thomas Lett
(74) *Attorney, Agent, or Firm* — Alexa L. Ashworth; Ryan, Mason & Lewis, LLP

(57) ABSTRACT

A method for providing a remote user with an experience in an environment, comprising building a three-dimensional (3D) model of the environment, capturing one or more video feeds of at least a portion of the environment using one or more cameras in the environment, mapping the one or more video feeds onto one or more planes in the 3D model, providing a view of the mapped one or more video feeds on the one or more planes in the 3D model through a display device viewed by the remote user, capturing a gestural input from the remote user, and applying the gestural input to the portion of the environment.

16 Claims, 10 Drawing Sheets

(56) References Cited

OTHER PUBLICATIONS

C. Cruz-Neira et al., "The Cave: Audio Visual Experience Automatic Virtual Environment," Communications of the ACM, Jun. 1992, pp. 64-72, vol. 35, No. 6.
Kikuo Asai, "The Role of Head-Up Display in Computer-Assisted Instruction," National Institute of Multimedia Education, Japan, Oct. 2008, pp. 31-48.
"Kinect," https://en.wikipedia.org/wiki/Kinect, Accessed: Dec. 12, 2015, 18 pages.
"Oculus Rift," https://en.wikipedia.org/wiki/Oculus_Rift, Accessed: Dec. 12, 2015, 13 pages.
B. S. Babu, "Cognitive Agents," http://pet.ece.iisc.ernet.in/sathish/cognitive.pdf, Accessed: Oct. 18, 2015, 19 pages.
E. Carson, "Nine Industries Using Virtual Reality" http://www.techrepublic.com/article/9-industries-using-virtual-reality/, Mar. 2015, 9 pages.
http://www.oblong.com/g-speak/, Accessed: Oct. 25, 2015, 3 pages.
https://www.microsoft.com/microsofthololens/enus, Accessed: Dec. 15, 2015, 7 pages.
I. Sutherland, "A Head-Mounted Three Dimensional Display," Fall Joint Computer Conference, AFIPS Conference Proceedings, Dec. 1968, pp. 757-764, vol. 33.
https://www.oculus.com/en-us/rift/, Accessed: Oct. 11, 2015, 10 pages.
H. Chen et al., "An Ontology for Context-Aware Pervasive Computing Environments," The Knowledge Engineering Review Journal, vol. 18, No. 3, Sep. 2003, pp. 197-207.
D. A. Bowman et al., "An Evaluation of Techniques for Grabbing and Manipulating Remote Objects in Immersive Virtual Environments," 1997 Symposium on Interactive 3D Graphics, 1997, pp. 35-38.
J. O. Kephart et al., "A Symbiotic Cognitive Computing Perspective on Autonomic Computing," Autonomic Computing (ICAC), IEEE International Conference, Jul. 2015, pp. 109-114.
P. Halamkar et al., "A Review on Virtual Reality," International Journal of Computer Science Issues, Nov. 2012, pp. 325-330, vol. 9, Issue 6, No. 1.
L. A. Nguyen et al., "Virtual Reality Interfaces for Visualization and Control of Remote Vehicles," Autonomous Robots, vol. 11, 2001, pp. 59-68.
C. Cruz-Neira et al., "Surround-Screen Projection-Based Virtual Reality: The Design and Implementation of the Cave," Computer Graphics and Interactive Techniques, vol. 20, 1993, pp. 135-142.
H. Soltau et al., "The IBM Attila Speech Recognition Toolkit," Spoken Language Technology Workshop (SLT), IEEE, Dec. 2010, pp. 97-102.

\* cited by examiner

100

US 9,785,741 B2

IMMERSIVE VIRTUAL TELEPRESENCE IN A SMART ENVIRONMENT

TECHNICAL FIELD

The field generally relates to providing a remote user with an experience in an environment and, in particular, an experience of immersive virtual telepresence in a smart environment.

BACKGROUND

The use of technologically advanced conference rooms has increased in recent years. In order to support more fluid interaction with users of such rooms, these conference rooms may employ high bandwidth audio-visual equipment that may permit interactivity using, for example, voice and/or gestural input. With known systems, participants remote from a technologically advanced conference room are passive and are not able to interact with components of the room.

Virtual reality (VR) has been defined as an experience where a person is "surrounded by a three dimensional computer-generated representation, and is able to move around in the virtual world and see it from different angles, to reach into it, grab it, and reshape it." See Rheingold, H., *Virtual Reality*, New York: Summit, 1991. VR head-mounted display devices such as the Oculus® Rift® DK2 head-mounted display system, sold by Oculus VR, LLC of Menlo, Park, Calif., provide immersive experiences in virtual environments suitable for gaming and the more direct experiencing of stories. Companies have been working on consumer versions of VR headsets with the gaming audience as their target, using virtual environments that lack correspondence with the real world.

SUMMARY

According to an exemplary embodiment of the present invention, a method for providing a remote user with an experience in an environment, comprises building a three-dimensional (3D) model of the environment, capturing one or more video feeds of at least a portion of the environment using one or more cameras in the environment, mapping the one or more video feeds onto one or more planes in the 3D model, providing a view of the mapped one or more video feeds on the one or more planes in the 3D model through a display device viewed by the remote user, capturing a gestural input from the remote user, and applying the gestural input to the portion of the environment.

According to an exemplary embodiment of the present invention, a system for providing a remote user with an experience in an environment comprises a memory and at least one processor coupled to the memory, wherein the at least one processor is configured to build a three-dimensional (3D) model of the environment, capture one or more video feeds of at least a portion of the environment using one or more cameras in the environment, map the one or more video feeds onto one or more planes in the 3D model, provide a view of the mapped one or more video feeds on the one or more planes in the 3D model through a display device viewed by the remote user, capture a gestural input from the remote user, and apply the gestural input to the portion of the environment.

According to an exemplary embodiment of the present invention, a computer program product for providing a remote user with an experience in an environment comprises a computer readable storage medium having program instructions embodied therewith, the program instructions executable by a processor to cause the processor to perform a method comprising building a three-dimensional (3D) model of the environment, capturing one or more video feeds of at least a portion of the environment using one or more cameras in the environment, mapping the one or more video feeds onto one or more planes in the 3D model, providing a view of the mapped one or more video feeds on the one or more planes in the 3D model through a display device viewed by the remote user, capturing a gestural input from the remote user, and applying the gestural input to the portion of the environment.

These and other exemplary embodiments of the invention will be described or become apparent from the following detailed description of exemplary embodiments, which is to be read in connection with the accompanying drawings.

BRIEF DESCRIPTION OF THE DRAWINGS

Exemplary embodiments of the present invention will be described below in more detail, with reference to the accompanying drawings, of which.

DETAILED DESCRIPTION

Exemplary embodiments of the invention will now be discussed in further detail with regard to providing a remote user with an experience in an environment and, in particular, to immersive virtual telepresence in a smart environment that allows remote participants to access or control the technological functions and/or capabilities of environments in which the remote participants are not present. This invention may, however, be embodied in many different forms and should not be construed as limited to the embodiments set forth herein.

Embodiments of the present invention relate to systems and methods that provide an immersive experience to a remote participant collaborating with other participants using a technologically equipped room, such as, for example, a "smart" conference room.

As used herein, a "smart room," "smart meeting room" or "smart conference room" can refer to an environment that offers the power of advanced computing to assist users in complex tasks. The room is designed as a space for humans and systems to collaborate in a symbiotic cognitive computing experience, where humans are given the opportunity to, for example, identify important problems and apply value judgements, while the computing systems, for example, seamlessly perform analytics on data (e.g., big data) and run simulations.

Figure 1:
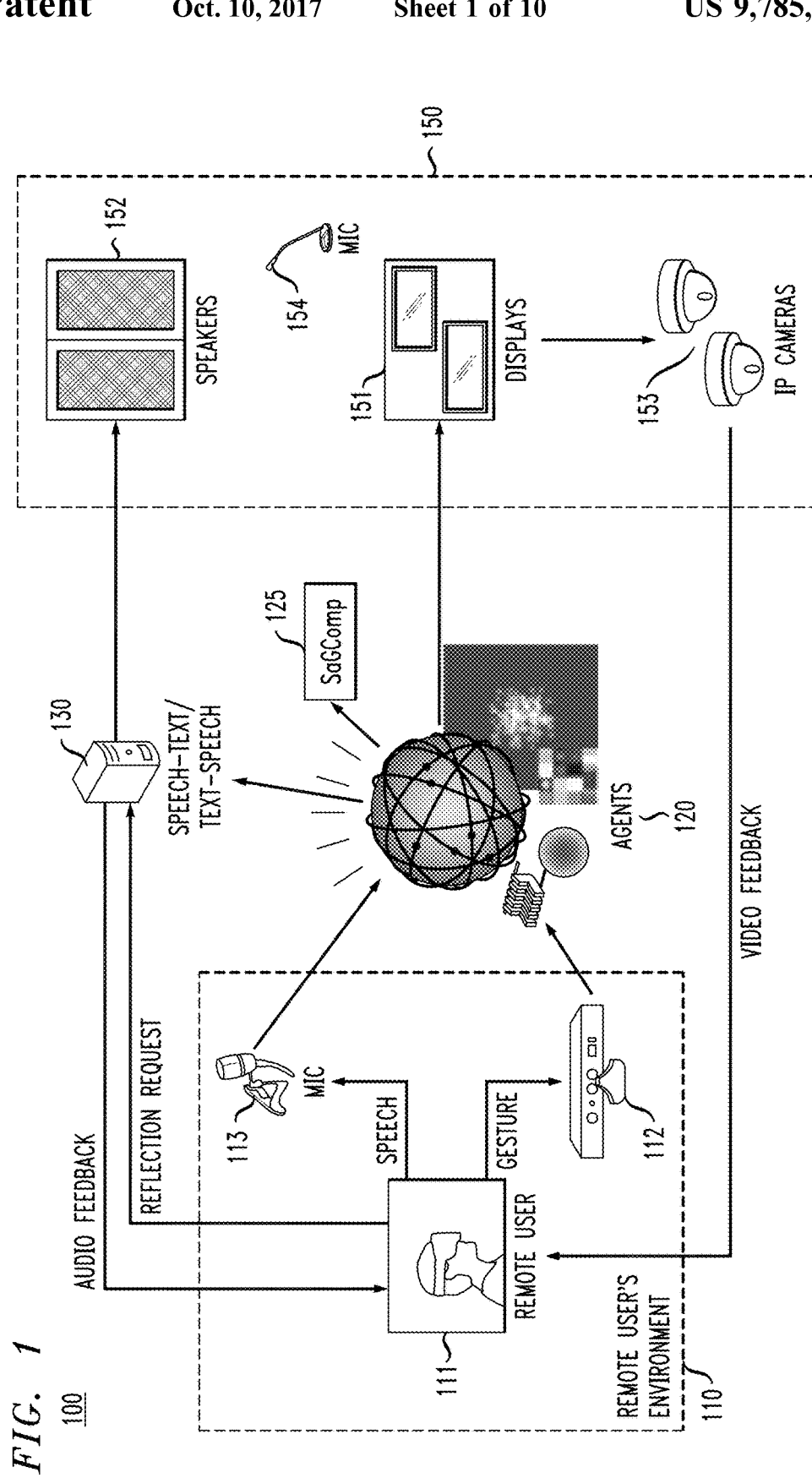
FIG. 1 is a block diagram of a system for providing a remote user with an experience in an environment, according to an exemplary embodiment of the present invention.

FIG. 1 is a block diagram of a system for providing a remote user with an experience in an environment, according to an exemplary embodiment of the present invention. As shown in FIG. 1 by lines and/or arrows, the components of the system 100 are operatively coupled to each other via, for example, physical connections, such as wired and/or direct electrical contact connections, and wireless connections, such as, for example, WiFi, BLUETOOTH, IEEE 802.11, and/or networks, including but not limited to, a local area network (LAN), wide area network (WAN), cellular network, ad hoc networks, WANET, satellite network or the Internet.

By way of non-limiting example, in accordance with an embodiment of the present invention, referring to FIG. 1, a smart room, smart meeting room or smart conference room 150 can be equipped with a variety of devices and sensors, such as, for example, displays 151, speakers 152, cameras 153 and microphones 154. For example, referring to FIG. 3, a front of a room 150 can include an array 151a of monitors. The room 150 can further include, but is not limited to, monitors on a periphery of the room, such as monitors 151b and 151c on right and left sides of the room. In accordance with an embodiment, the monitors 151b and 151c can be movable to anywhere along the periphery of the room. The back of the room 150 can also include, but is not limited to, a monitor 151d.

Figure 4A:
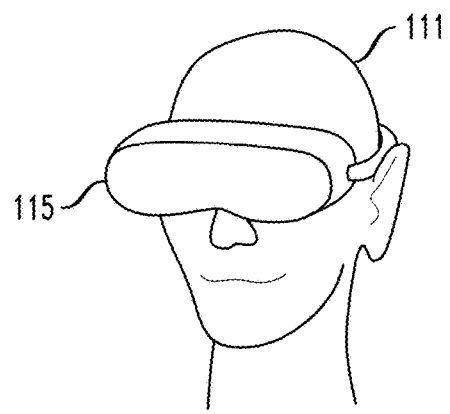
FIG. 4A illustrates a remote user wearing a head-mounted display device, according to an exemplary embodiment of the present invention.
Figure 5A:
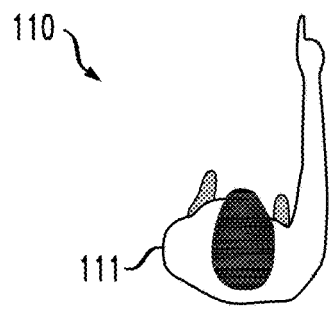
FIG. 5A illustrates a remote user making a gesture, according to an exemplary embodiment of the present invention.
Figure 5B:
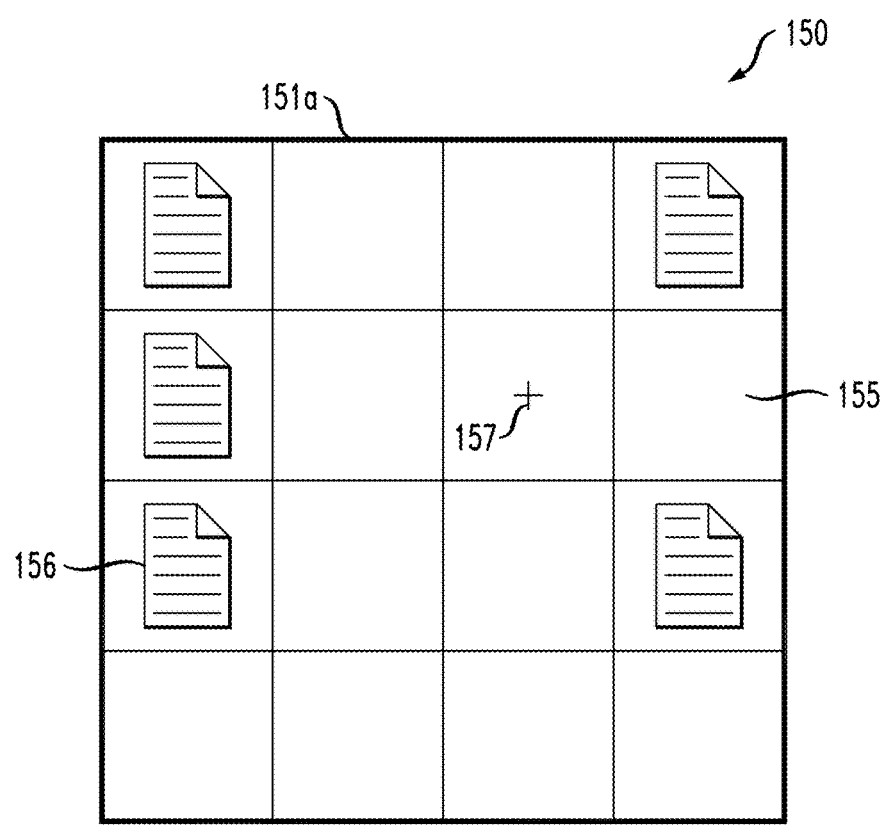
FIG. 5B illustrates an array of monitors on which content and an indicator are displayed, according to an exemplary embodiment of the present invention.

In accordance with an embodiment of the present invention, referring to FIGS. 5A and 5B, content 156 can be moved from monitor to monitor 155 with the aid of a cross-monitor pointing device held by a user 111 in the user's hand, referred to herein as a "wand." The movement of the wand is electronically linked to corresponding movement of a pointer 157, like a mouse pointer or cursor, which is visible on the array 151a by individuals in the room 150, and, virtually, through a head-mounted display, such as head-mounted display 115 worn by remote user 111 as shown in FIG. 4A.

As used herein, a "VR head-mounted display device," "head-mounted display device" or "head-mounted display" can refer to a display device that users wear on their heads or as part of a helmet, which has a display optic in front of one or each of the user's eyes. The display units can include, for example, a cathode ray tube (CRT), a liquid crystal display (LCD), liquid crystal on silicon (LCos), or organic light emitting diode (OLED) devices. In accordance with an embodiment of the present invention, the head-mounted display device is capable of complete rotational and positional tracking of the user's head. Positional tracking is performed by, for example, an external infra-red (IR) based tracking unit separated from but in proximity to the head-mounted display device, such as on a table or desk in a room with the user. The rotational and positional tracking allows for use of the head-mounted display device while standing and walking around in a room. An example of a commercially available head-mounted display device is the Oculus® Rift® DK2 head-mounted display system sold by Oculus VR, LLC of Menlo Park, Calif. While the embodiments of the invention are discussed in connection with head-mounted display devices, it is contemplated that other display devices may be used, such as, for example, free standing display devices adjacent and/or on multiple sides of a remote user.

A user 111 can view the movement of the pointer 157 across different monitors 155 within the array 151a or on the other displays 151b, 151c and 151d through the head-mounted display device 115, and by directing the pointer 157 on content 156 via movement of the wand, can move content 156 from one monitor 155 to another monitor 155, or to the other displays 151b, 151c and 151d. According to an embodiment of the present invention, by combining pointing, interpreted with the aid of a depth sensor (such as that provided by the Microsoft® Kinect®, sold by Microsoft Corporation of Redmond, Wash.), and voice command understandable by the system (e.g., "move this here"), a remote user 111 can move the content by pointing at the content and locations to where the remote user 111 wants to move the content, and stating the voice command. The content (e.g., content 156) can be moved across different monitors 155 within an array 151a or to the other displays 151b, 151c and 151d.

Alternatively, movement of content can be performed via a joint effort between a remote user, and a local user in the room 150. For example, using the pointing and a voice command able to be heard by the local user, the remote user 111 can state the voice command (e.g., "move this"), and point to the content 156 where the remote user 111 wants to move the content 156 from. The pointing would be visible to the local user via the pointer 157 in the room 150. Then, the local user can move the content 156 as directed by the remote user to a location of the local user's choosing. Accordingly, the system can operate with the remote user 111 taking complete control of the room, or where the remote user 111 works with the room in tandem with local occupants of the room 150. The remote set-up includes the tracking system 112 having a depth-sensor that can be used to detect what the remote user 111 is pointing at, and project the pointer 157 on a screen for the local users in the room to see. The remote user 111 can also see the pointer 157 through their head-mounted display device 115. In another alternative, content 156 can also be moved programmatically (i.e., using program code).

A smart room, smart meeting room or smart conference room 150 can be outfitted with a plurality of speakers 152 and microphones 154. Referring to FIG. 1, the system 100 further includes a speech-to-text (speech recognition) and text-to-speech transcription system 130. Using the speakers 152, local users in the room 150 can hear what the remote user 111 is saying just like in any teleconferencing system. However, unlike conventional systems, according to an embodiment of the present invention, the system transcribes what is being said by a remote user by virtue of the speech-to-text component of the transcription system 130 (also known as a speech recognition component) that runs directly on the voice output of the remote user 111. In other words, the speech-to-text component does not run on the degraded voice output as picked up by a teleconferencing system. As a result, the system can respond to the combination of pointing and speech by the remote users 111 to understand their intent and respond accordingly.

In addition, via the speech-to-text component, the local users in a room 150 can receive text outputs and devices in a room 150 can function in response to what is being said by a remote user 111 (e.g., respond to voice commands). Also, a complementary text-to-speech component of transcription system 130 can synthesize appropriate voice feedback for the remote user 111 from, for example, the room itself or local users in the room 150.

In accordance with an embodiment of the present invention, software applications for the room can be built as distributed multi-agent systems. A multi-agent system (MAS) can refer to a computerized system including a plurality of software agents that can interact with each other within an environment to solve problems that may be difficult or impossible for an individual agent to solve. One or more of the software agents 120 can be "cognitive agents." As used herein, a cognitive agent can refer to a software entity which functions continuously and autonomously in an environment, is capable of carrying out activities in a flexible and intelligent manner, is responsive to environmental changes, learns from experience, communicates and cooperates with other agents, is proactive, exhibits opportunistic and goal-oriented behavior, and takes an initiative when appropriate.

Traditional solutions for virtual collaboration, such as video conferencing or chat rooms, do not allow remote participants to access or control the technological functions and/or capabilities of rooms in which the remote participants are not present. In accordance with an embodiment of the present invention, a system for immersive virtual telepresence in a smart conference room is provided that does allow such access to and control of the technological functions and/or capabilities of the rooms in which the remote participants are not present. The embodiments of the present invention permit a user that is not present in a room to have experiences similar to what is experienced by occupants in the room itself, by providing an immersive experience for remote participants while also enabling them to control aspects of the smart conference room. While embodiments of the present invention are discussed in connection with conference and/or meeting rooms, it is to be understood that the embodiments of the present invention are not necessarily limited thereto, and may be applicable to other environments, such as for example, medical operating room, vehicle, military, industrial or other environments where remote participants may benefit from an immersive experience and control of the remote environment. By way of non-limiting example, the embodiments of the present invention may be applicable to the healthcare, automotive, aeronautics, education, tourism, military, space exploration and law enforcement fields, in both training and actual real-world scenarios.

Figure 2:
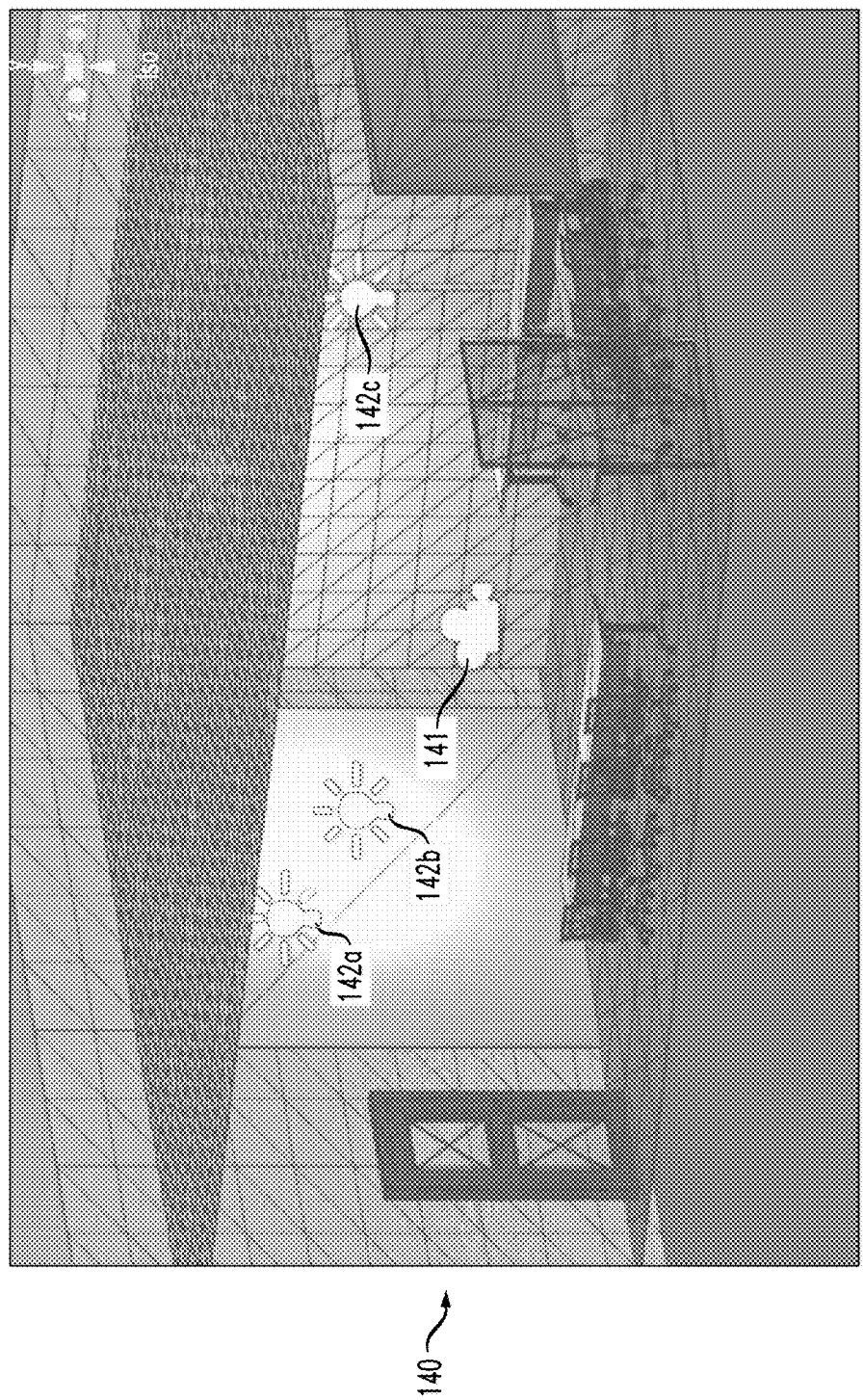
FIG. 2 illustrates a 3D model of a room, according to an exemplary embodiment of the present invention.
Figure 3:
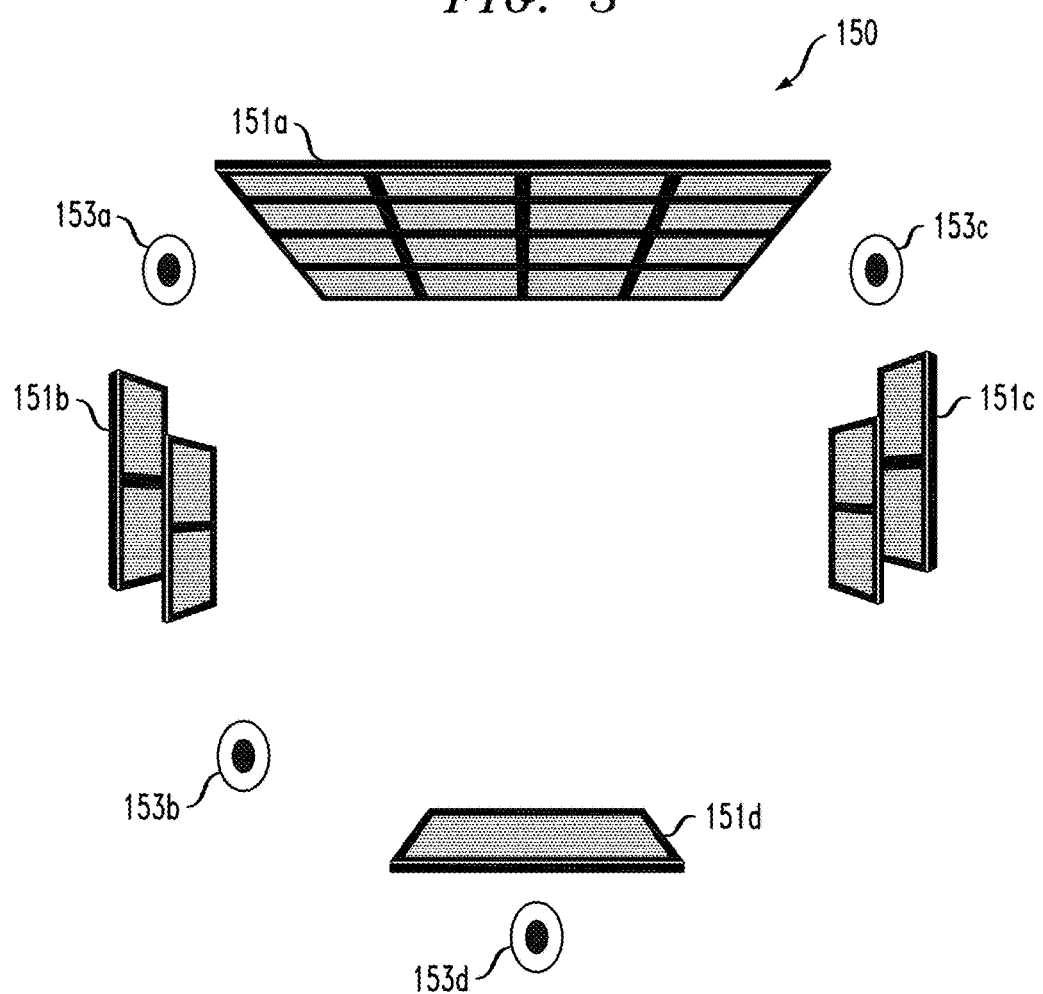
FIG. 3 illustrates a layout of a room including displays and cameras, according to an exemplary embodiment of the present invention.
Figure 4B:
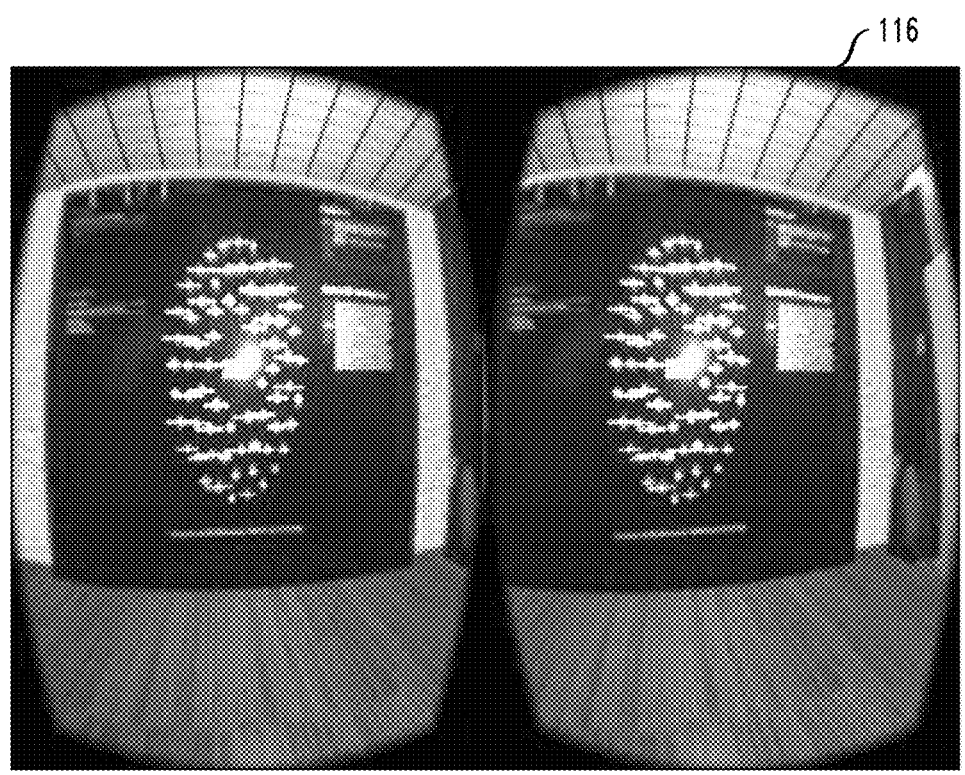
FIG. 4B illustrates a view through a head-mounted display device, according to an exemplary embodiment of the present invention.

Dynamic environments such as conference rooms with people moving around and content on screens changing, can require frequent updates for a remote participant, so that the remote user does not miss or lose important information about what is transpiring in the room. Embodiments of the present invention utilize live video feeds from cameras 153, for example, internet protocol (IP) cameras, to overlay the dynamics of an environment on a static three-dimensional (3D) model 140 of the room 150. The cameras, for example, cameras 153a, 153b, 153c and 153d as shown in FIG. 3, capture the content displayed on screens as well as people and objects in the room 150, and this content is projected on the walls of the 3D model 140. For example, FIG. 2 shows a 3D model 140. Embodiments of the present invention project imagery onto the walls of the 3D model 140 of the room, and render views of the room 150 for a remote user 111 in a perspectively correct way using a VR head-mounted display device 115. For example, referring to FIG. 4B, the view 116 can be of a display on a wall. The view can be of any portion of the room 150 based on a physical orientation of the user 111 calibrated with the 3D model 140, and drawing a correspondence between the physical orientation of the remote user 111 and a vantage point in the room 150. For example, as shown in FIGS. 5A and 5B, after a calibration, the system may interpret a user's position as being oriented in the direction of array 151a, so that the array 151a is displayed via the head-mounted display device 115 as if the user 111 is looking directly at the array 151a. To provide an accurate and calibrated view of the captured content, appropriate transformations with respect to, for example, size, scale and aspect ratio, are performed in order to map the video feed from cameras 153 onto one or more planes of the 3D model 140.

In accordance with an embodiment of the present invention, an immersive experience for remote participants in a smart conference room is provided via a multi camera network and a head-mounted display, and enables gestural interaction from a remote location to directly access and/or modify content in the room. The embodiments of the present invention provide for real-time remote control of an actual physical environment (e.g., a smart conference room) using a VR head-mounted display device.

As used herein, term "real-time" refers to output within strict time constraints. Real-time output can be understood to be instantaneous or in the order of milliseconds or microseconds. Of course, it should be understood that depending on the particular temporal nature of the system in which an embodiment of the invention is implemented, other appropriate timescales that provide approximately contemporaneous performance and output can be achieved.

When the system is used in conjunction with local users of the room, e.g. in a video teleconferencing type of use-case, embodiments of the present invention provide for not only incorporating a 3D model of the room, superimposing images on the relevant screens or 2D planes (walls), but also considering the seating locations of participants and rendering these seated participants within the 3D setting. In accordance with an embodiment of the present invention, the system can perform face recognition, and/or once various participants log into the system, including self-identifying and submitting a way of contacting them (e.g., via email), the system can send custom material to the specific people in the room and/or to the remote participant(s) that have logged into or have been recognized by the system. Material can also be sent to the local or remote participants at the discretion of the smart meeting room.

Referring to FIG. 1, the remote user 111 interacts with the agents 120 using, for example, speech and gestures. A control flow of the system 100 is depicted in FIG. 1. In accordance with an embodiment of the present invention, speech signals of the remote user 111 are picked up by microphones 113 and can be transcribed into word-by-word transcripts using a speech-text component of transcription system 130. An example of a speech-text system is the IBM® Attila™ speech recognition system offered by International Business Machines Corporation of Armonk, N.Y. The system 100 can also recognize gestures of the remote user 111, such as, for example, arm movements like pointing and waving. The gesture recognition can be performed using skeletal tracking of body joints by a tracking system 112, including, but not limited to a local depth sensing system. An example of a commercially available tracking system is the Microsoft® Kinect® system in conjunction with Kinect® software for Windows® SDK, sold by Microsoft Corporation of Redmond, Wash. According to an embodiment of the present invention, using 3D coordinates of body joints, the system estimates a pointing direction as the intersection of a line joining the head center, based on eye position of the remote user 111, to the most outstretched position of the remotes user's hand, with the virtual screen plane. The output of the interaction is displayed on the room display screens, for example, monitors 155 of array 151a as the pointer 157, also referred to herein as a cursor. Live feeds are provided to the head-mounted display device 115 from strategically situated cameras 153, such as, for example, video cameras 153a, 153b, 153c and 153d in the room 150, to provide video feedback to the remote user 111 regarding where the cursor 157 is on any display, as well as a possibly changed state of virtual content shown on the displays. As noted above, the cameras 153 can include IP cameras. In addition, the displays can be present on array 151a, as well as displays 151b, 151c and 151d.

Referring to FIG. 2, to provide a representative immersive experience to remote participants, a 3D model 140 of the room 150 is created. Common objects in the room 150, such as tables and chairs, can be inserted into the model. In accordance with an embodiment, a virtual camera 141, is initially inserted in the center of the 3D model 140 and thereafter the camera is controlled by the user's head movements as tracked by the head-mounted display device 115. The orientation of the virtual camera 141 indicates the perspective from which the scene for the remote user 111 is being rendered. The light bulb icons 142a, 142b, 142c indicate the location of virtual light sources in the room 150.

The 3D model 140 allows the system to render in real time a close facsimile to what a user in the real room would see as they take steps toward or away from objects in the room 150, such as displays 151, or turn their head. Although it may not be possible to recreate an entire 3D model of the room as the dynamics of the room change, the system and/or designers of the system can make determinations to change only those the parts of the scene that are likely of most consequence to the remote user 111. For example, according to an embodiment of the present invention, the system is configured to capture information content on display screens 151 and anything near the periphery of the room 150 through strategically placed IP cameras 153, and project/map corresponding video feeds from the IP cameras 153 onto the planes in the 3D model 140 that are associated with the walls of the room (e.g., vertical planes). This manner of capturing the dynamics allows the remote user 111 to see and access content displayed on the screens and also to see most meeting participants, given the U-shaped seating arrangement that can be typical for occupants of conference rooms. The video feeds from the IP cameras may be real-time video feeds.

In addition to controlling content via gesture as sensed by the tracking system 112, the remote user 111 also receives audio feedback, such as, for example, direct speech output by the smart conference room. According to an embodiment of the present invention, before beginning the remote interaction, the remote user's system sends a reflection request to a text-to-speech component, which then echoes synthesized speech sent to the room speakers 152, to speakers supporting the remote user 111. On the whole, the system 100 aims to offer an immersive experience for remote users that is not too dissimilar from that of local users of the room 150.

In accordance with an embodiment of the present invention, speech transcript and skeletal coordinates are synchronously sent to a speech and gesture comprehension (SaGComp) module 125 using a distributed messaging protocol, which uses, for example, a publish-subscribe messaging pattern to facilitate distributed messaging among various agents 120. An example of a distributed messaging protocol is the ZeroMQ® pubsub messaging library offered by iMatix Corporation of Brussels, Belgium. The SaGComp module 125 includes logic to transform speech and gestural input into a request to modify content displayed on any of the displays 151 in the room 150 and/or to add/remove content to/from one of the system's virtual artifacts. Typical virtual artifacts include data visualizations of different varieties, including graphs and charts.

Figure 6A:
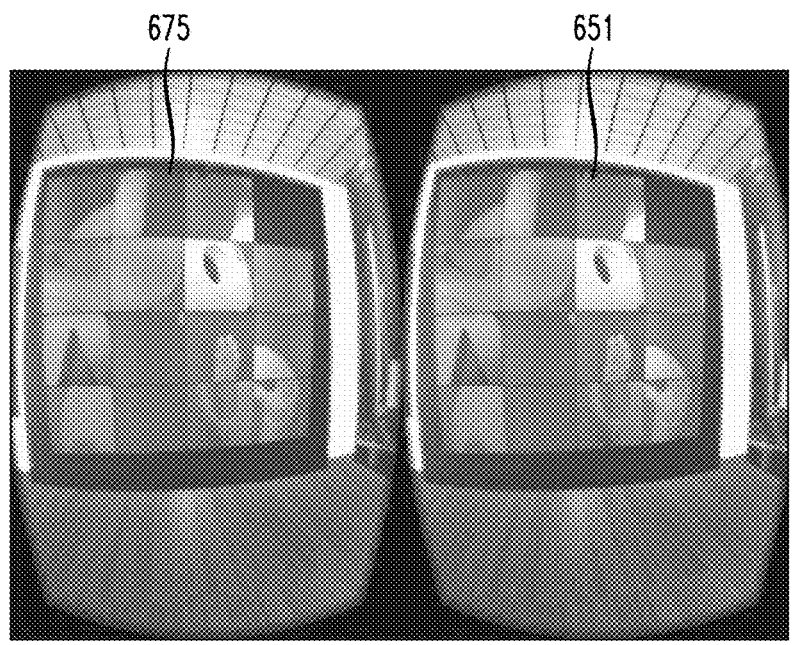
FIGS. 6A and 6B illustrate an example of an immersive experience of a remote user collaborating with a local (in-room) user to complete a task, according to an exemplary embodiment of the present invention.
Figure 6B:
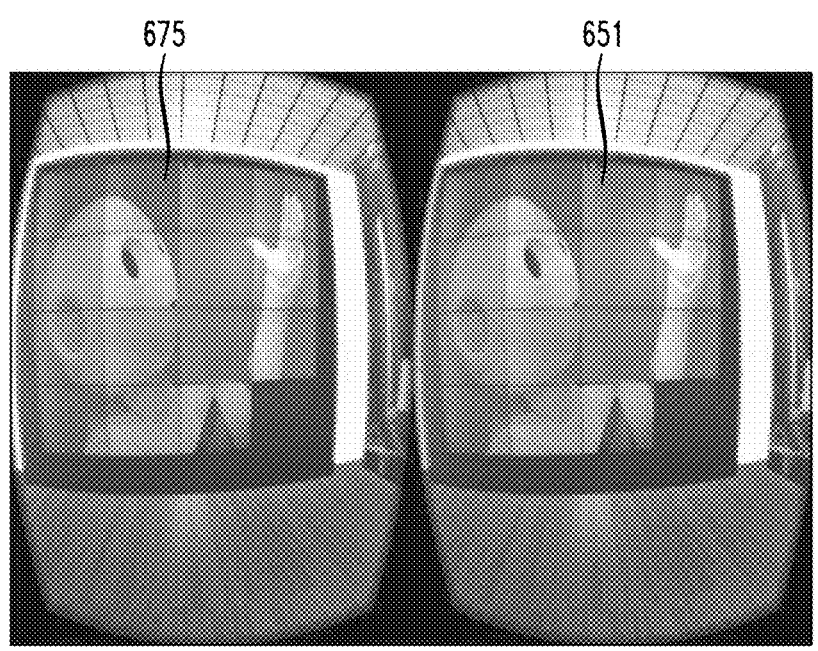

FIGS. 6A and 6B illustrate an example of an immersive experience of a remote user collaborating with a local (in-room) user to complete a task. In this example, a remote user 111 collaboratively solves a picture puzzle game 675 displayed on a 4×4 display screen 651, with each element of the 4×4 array comprising a puzzle piece, as shown in FIGS. 6A and 6B. FIGS. 6A and 6B show the screen 651 as on a wall of the 3D model 140 as would be seen through the head-mounted display device 115. The actual screen 651 is on a wall in the room where the local user is present. The remote user 111 can point and speak to give directions regarding where to move the puzzle pieces, while the local user actually moves the puzzle pieces in response, using an appropriate user interface configured to control movement of the puzzle pieces on the screen 651. The gestures of the user 111, including pointing at different puzzle pieces, and indicating where on the 4×4 array to move the puzzle pieces, are electronically linked to a cursor, or some other type of indicator displayed on the screen 651 in the room. Accordingly, the local user is able to directly see the cursor as it is moved by the user 111, and the user 111 is able to see the movement of the cursor via the head-mounted display device, which displays the video feed of the screen 651 from one or more cameras, like cameras 153, in the room.

Figure 7:
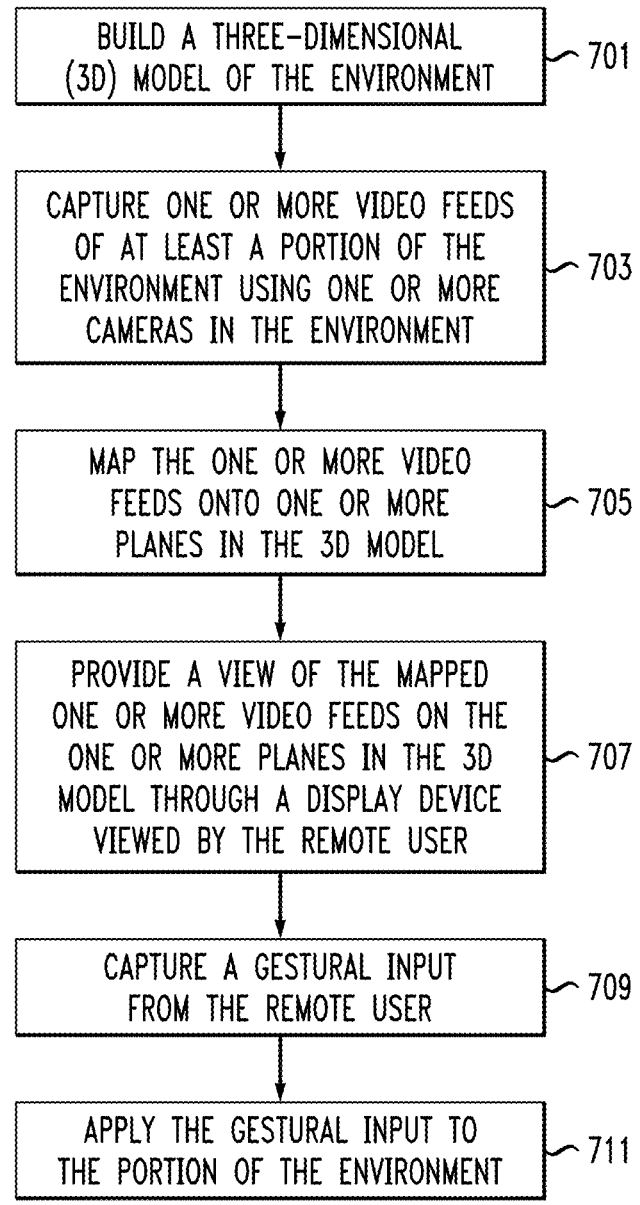
FIG. 7 is a flow diagram of a process for providing a remote user with an experience in an environment, according to an exemplary embodiment of the invention.

FIG. 7 is a flow diagram of a process for providing a remote user with an experience in an environment, according to an exemplary embodiment of the invention. Referring to FIG. 7, the process 700 includes, at block 701, building a 3D model of the environment. The environment can include, but is not limited to, a smart room, such as, for example, a smart conference room. The process 700 further includes, at block 703, capturing one or more video feeds of at least a portion of the environment using one or more cameras in the environment. As noted above, the cameras can be IP cameras strategically positioned in the environment and can provide real-time video feeds. At block 705, the process also includes mapping the one or more video feeds onto one or more planes in the 3D model, such as for example vertical planes that the remote user may be oriented toward. A physical orientation of the remote user may be calibrated with respect to the 3D model, and correspond to a vantage point in the environment.

The process 700 further includes, at block 707, providing a view of the mapped one or more video feeds on the one or more planes in the 3D model through a display device viewed by the remote user. The display device can include, but is not limited to, a head mounted display device worn by the remote user.

The process also includes, at block 709, capturing a gestural input from the remote user, and, at block 711, applying the gestural input to a portion of the environment. Applying the gestural input to a portion of the environment can comprise electronically linking the gestural input to an indicator, such as a pointer or cursor, displayed on a screen in the environment, wherein movement of the indicator on the screen is synchronized with the gestural input. The portion of the environment can comprise at least one display displaying electronic content, wherein applying the gestural input to the portion of the environment comprises electronically linking the gestural input to the electronic content so that the gestural input can affect the movement of the electronic content, such as, for example, the movement of a document, slide, portion of text, web page, etc. between monitors. The remote user views the movement of the electronic content through the display device while a local user in the environment views the movement on the at least one display.

The process may also comprise capturing a voice input from the remote user, and applying the voice input in the environment to control at least one object in the environment. One or more users in the environment can be recognized using, for example, facial recognition and/or log in procedures, and rendered in the 3D model.

Embodiments of the present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 8:
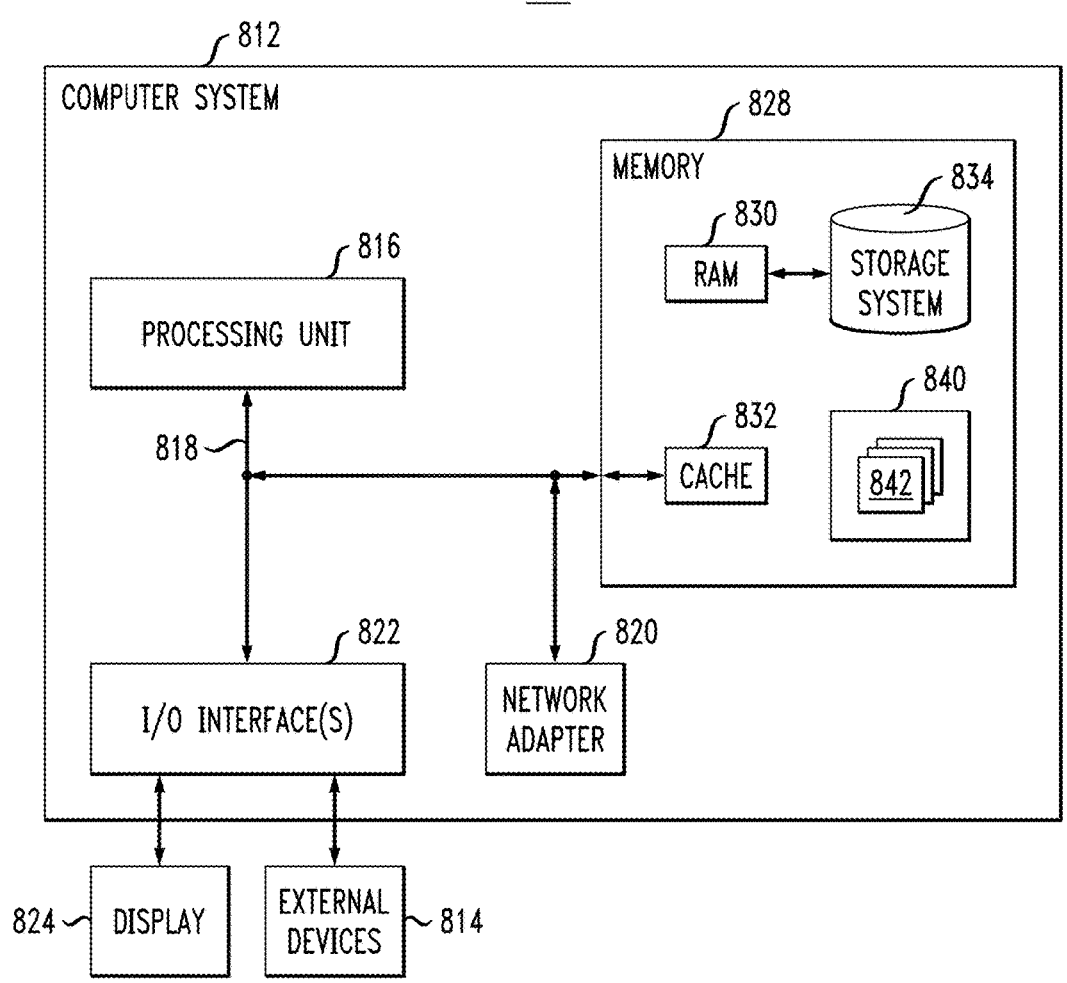
FIG. 8 illustrates a computer system in accordance with which one or more components/steps of the techniques of the invention may be implemented, according to an exemplary embodiment of the invention.

One or more embodiments can make use of software running on a general-purpose computer or workstation. With reference to FIG. 8, in a computing node 810 there is a computer system/server 812, which is operational with numerous other general purpose or special purpose computing system environments or configurations. Examples of well-known computing systems, environments, and/or configurations that may be suitable for use with computer system/server 812 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 812 may be described in the general context of computer system executable instructions, such as program modules, being executed by a computer system. Generally, program modules may include routines, programs, objects, components, logic, data structures, and so on that perform particular tasks or implement particular abstract data types. Computer system/server 812 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 8, computer system/server 812 in computing node 810 is shown in the form of a general-purpose computing device. The components of computer system/server 812 may include, but are not limited to, one or more processors or processing units 816, a system memory 828, and a bus 818 that couples various system components including system memory 828 to processor 816.

The bus 818 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system/server 812 typically includes a variety of computer system readable media. Such media may be any available media that is accessible by computer system/server 812, and it includes both volatile and non-volatile media, removable and non-removable media.

The system memory 828 can include computer system readable media in the form of volatile memory, such as random access memory (RAM) 830 and/or cache memory 832. The computer system/server 812 may further include other removable/non-removable, volatile/nonvolatile computer system storage media. By way of example only, storage system 834 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 818 by one or more data media interfaces. As depicted and described herein, the memory 828 may include at least one program product having a set (e.g., at least one) of program modules that are configured to carry out the functions of embodiments of the invention. A program/utility 840, having a set (at least one) of program modules 842, may be stored in memory 828 by way of example, and not limitation, as well as an operating system, one or more application programs, other program modules, and program data. Each of the operating system, one or more application programs, other program modules, and program data or some combination thereof, may include an implementation of a networking environment. Program modules 842 generally carry out the functions and/or methodologies of embodiments of the invention as described herein.

Computer system/server 812 may also communicate with one or more external devices 814 such as a keyboard, a pointing device, a display 824, etc., one or more devices that enable a user to interact with computer system/server 812, and/or any devices (e.g., network card, modem, etc.) that enable computer system/server 812 to communicate with one or more other computing devices. Such communication can occur via Input/Output (I/O) interfaces 822. Still yet, computer system/server 812 can communicate with one or more networks such as a local area network (LAN), a general wide area network (WAN), and/or a public network (e.g., the Internet) via network adapter 820. As depicted, network adapter 820 communicates with the other components of computer system/server 812 via bus 818. It should be understood that although not shown, other hardware and/or software components could be used in conjunction with computer system/server 812. Examples, include, but are not limited to: microcode, device drivers, redundant processing units, external disk drive arrays, RAID systems, tape drives, and data archival storage systems, etc.

It is understood in advance that although this disclosure includes a detailed description on cloud computing below, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Computing node 810 in FIG. 8 can be an example of a cloud computing node. Computing node 810 is only one example of a suitable cloud computing node and is not intended to suggest any limitation as to the scope of use or functionality of embodiments of the invention described herein. Regardless, computing node 810 is capable of being implemented and/or performing any of the functionality set forth hereinabove. It is also to be understood that computing node 810 is not necessarily a cloud computing node.

Figure 9:
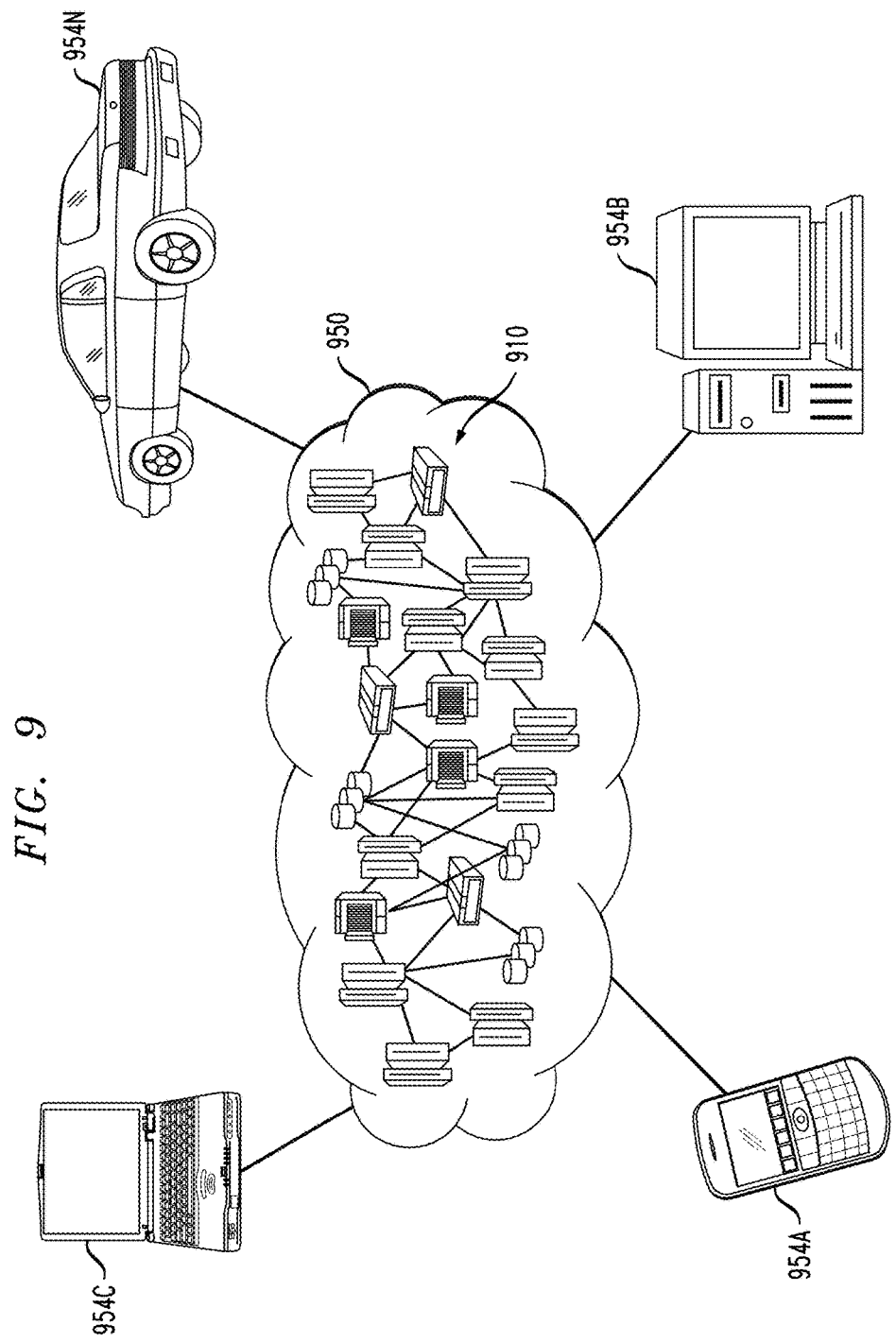
FIG. 9 depicts a cloud computing environment, according to an exemplary embodiment of the present invention.

Referring now to FIG. 9, illustrative cloud computing environment 950 is depicted. As shown, cloud computing environment 950 comprises one or more cloud computing nodes 910 with which local computing devices used by cloud consumers, such as, for example, a wearable device (not explicitly shown), a personal digital assistant (PDA) or cellular telephone 954A, desktop computer 954B, laptop computer 954C, and/or automobile computer system 954N may communicate. Nodes 910 may communicate with one another. They may be grouped (not shown) physically or virtually, in one or more networks, such as Private, Community, Public, or Hybrid clouds as described hereinabove, or a combination thereof. This allows cloud computing environment 950 to offer infrastructure, platforms and/or software as services for which a cloud consumer does not need to maintain resources on a local computing device. It is understood that the types of computing devices 954A-N shown in FIG. 9 are intended to be illustrative only and that computing nodes 910 and cloud computing environment 950 can communicate with any type of computerized device over any type of network and/or network addressable connection (e.g., using a web browser).

Figure 10:
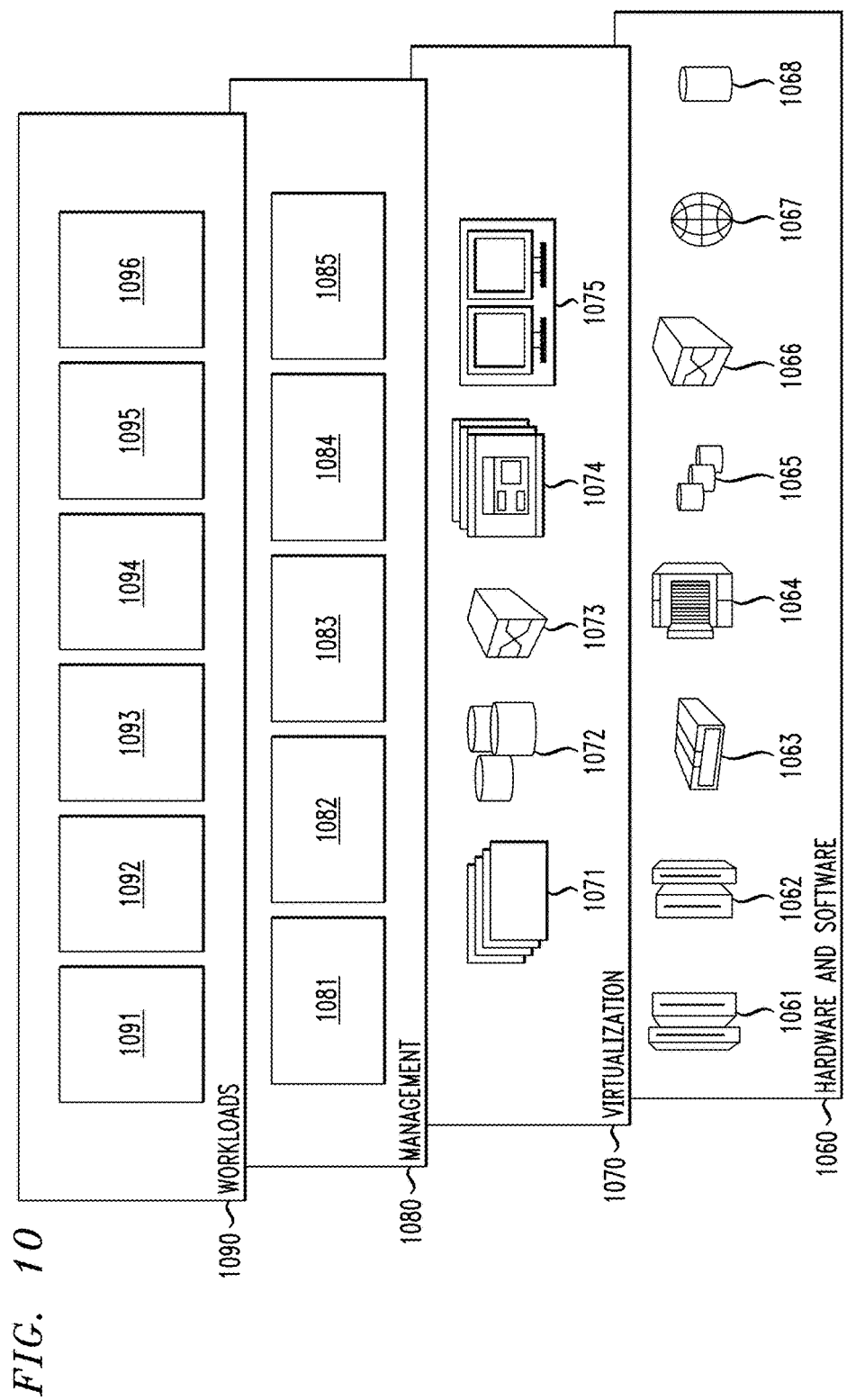
FIG. 10 depicts abstraction model layers, according to an exemplary embodiment of the invention.

Referring now to FIG. 10, a set of functional abstraction layers provided by cloud computing environment 950 (FIG. 9) is shown. It should be understood in advance that the components, layers, and functions shown in FIG. 10 are intended to be illustrative only and embodiments of the invention are not limited thereto. As depicted, the following layers and corresponding functions are provided:

Hardware and software layer 1060 includes hardware and software components. Examples of hardware components include: mainframes 1061; RISC (Reduced Instruction Set Computer) architecture based servers 1062; servers 1063; blade servers 1064; storage devices 1065; and networks and networking components 1066. In some embodiments, software components include network application server software 1067 and database software 1068.

Virtualization layer 1070 provides an abstraction layer from which the following examples of virtual entities may be provided: virtual servers 1071; virtual storage 1072;

virtual networks 1073, including virtual private networks; virtual applications and operating systems 1074; and virtual clients 1075.

In one example, management layer 1080 may provide the functions described below. Resource provisioning 1081 provides dynamic procurement of computing resources and other resources that are utilized to perform tasks within the cloud computing environment. Metering and Pricing 1082 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1083 provides access to the cloud computing environment for consumers and system administrators. Service level management 1084 provides cloud computing resource allocation and management such that required service levels are met. Service Level Agreement (SLA) planning and fulfillment 1085 provide pre-arrangement for, and procurement of, cloud computing resources for which a future requirement is anticipated in accordance with an SLA.

Workloads layer 1090 provides examples of functionality for which the cloud computing environment may be utilized. Examples of workloads and functions which may be provided from this layer include: mapping and navigation 1091; software development and lifecycle management 1092; virtual classroom education delivery 1093; data analytics processing 1094; transaction processing 1095; and remote user experience delivery 1096, which may implement the functionality described above with respect to FIGS. 1-9.

Embodiments of the present invention provide systems and methods for immersive virtual telepresence in a smart conference room using real-time video feeds from IP cameras and a head-mounted display device. Using a tracking system, remote users have the ability to control aspects of a room using gestures and/or speech. A 3D model of an immersive environment (e.g., smart conference room) is built and fed to a self-contained head-mounted display device. The content of displays seen in the heads-up display system is synced with the actual displays in the room. The remote user can interact with the content of the room using gestures as captured by a local depth sensing system and voice as captured by a local microphone and fed into an audio input system from the actual smart room. Any synthesized sound can be enabled for playing both in the room and in the remote facility via speakers at each location.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention. For example, although discussed in connection with conference rooms, embodiments of the present invention are not limited thereto, and may also be applied to, for example, such applications as remotely taking over for an airline pilot in distress, or for remotely assisting with or performing a surgical procedure.

What is claimed is:

1. A method for providing a remote user with an experience in an environment, comprising:
   building a three-dimensional (3D) model of the environment;
   capturing one or more video feeds of at least a portion of the environment using one or more cameras in the environment;
   mapping the one or more video feeds onto one or more planes in the 3D model;
   providing a view of the mapped one or more video feeds on the one or more planes in the 3D model through a display device viewed by the remote user;
   capturing a gestural input from the remote user, wherein the remote user is at a location remote from the environment; and
   applying the gestural input to the portion of the environment;
   wherein the portion of the environment comprises at least one display including a screen displaying electronic content;
   wherein applying the gestural input to the portion of the environment comprises electronically linking the gestural input to the electronic content so that the gestural input can affect movement of the electronic content displayed on the screen in the environment;
   wherein the movement of the electronic content displayed on the screen in the environment is synchronized with the gestural input of the remote user; and
   wherein the method is performed by at least one computer system comprising at least one memory and at least one processor coupled to the memory.

2. The method according to claim 1, wherein the electronic content comprises an indicator displayed on the screen in the environment, wherein movement of the indicator on the screen is synchronized with the gestural input of the remote user.

3. The method according to claim 1, further comprising calibrating a physical orientation of the remote user with the 3D model.

4. The method according to claim 1, further comprising corresponding a physical orientation of the remote user to a vantage point in the environment.

5. The method according to claim 1, wherein the remote user views the movement of the electronic content through the display device while another user in the environment views the movement on the at least one display.

6. The method according to claim 1, further comprising:
   capturing a voice input from the remote user; and
   applying the voice input in the environment to control at least one object in the environment.

7. The method according to claim 1, further comprising recognizing one or more users in the environment and rendering the one or more users in the 3D model.

8. The method according to claim 1, wherein the display device is a head mounted display device worn by the remote user.

9. The method according to claim 1, wherein the one or more video feeds include at least one real-time video feed.

10. A system for providing a remote user with an experience in an environment, comprising:
    a memory and at least one processor coupled to the memory, wherein the at least one processor is configured to:
    build a three-dimensional (3D) model of the environment;
    capture one or more video feeds of at least a portion of the environment using one or more cameras in the environment;
    map the one or more video feeds onto one or more planes in the 3D model;
    provide a view of the mapped one or more video feeds on the one or more planes in the 3D model through a display device viewed by the remote user;

capture a gestural input from the remote user, wherein the remote user is at a location remote from the environment; and apply the gestural input to the portion of the environment;

wherein the portion of the environment comprises at least one display including a screen displaying electronic content;

wherein, in applying the gestural input to the portion of the environment, the at least one processor is further configured to electronically link the gestural input to the electronic content so that the gestural input can affect movement of the electronic content displayed on the screen in the environment; and wherein the movement of the electronic content displayed on the screen in the environment is synchronized with the gestural input of the remote user.

11. The system according to claim 10, wherein the electronic content comprises an indicator displayed on the screen in the environment, wherein movement of the indicator on the screen is synchronized with the gestural input of the remote user.

12. The system according to claim 10, wherein the at least one processor is further configured to calibrate a physical orientation of the remote user with the 3D model.

13. The system according to claim 10, wherein the at least one processor is further configured to correspond a physical orientation of the remote user to a vantage point in the environment.

14. The system according to claim 10, wherein the remote user views the movement of the electronic content through the display device while another user in the environment views the movement on the at least one display.

15. The system according to claim 10, wherein the at least one processor is further configured to:

capture a voice input from the remote user; and apply the voice input in the environment to control at least one object in the environment.

16. A computer program product for providing a remote user with an experience in an environment, the computer program product comprising a computer readable storage medium having program instructions embodied therewith, the program instructions executable by a processor to cause the processor to perform a method comprising:

building a three-dimensional (3D) model of the environment;

capturing one or more video feeds of at least a portion of the environment using one or more cameras in the environment;

mapping the one or more video feeds onto one or more planes in the 3D model;

providing a view of the mapped one or more video feeds on the one or more planes in the 3D model through a display device viewed by the remote user;

capturing a gestural input from the remote user, wherein the remote user is at a location remote from the environment; and applying the gestural input to the portion of the environment;

wherein the portion of the environment comprises at least one display including a screen displaying electronic content;

wherein applying the gestural input to the portion of the environment comprises electronically linking the gestural input to the electronic content so that the gestural input can affect movement of the electronic content displayed on the screen in the environment; and wherein the movement of the electronic content displayed on the screen in the environment is synchronized with the gestural input of the remote user.

* * * * *